(12) United States Patent
Choi

(10) Patent No.: US 10,792,163 B2
(45) Date of Patent: Oct. 6, 2020

(54) SPINAL IMPLANT

(71) Applicant: Gun Choi, Pohang-si (KR)

(72) Inventor: Gun Choi, Pohang-si (KR)

( * ) Notice: Subject to any disclaimer, the term of this patent is extended or adjusted under 35 U.S.C. 154(b) by 3 days.

(21) Appl. No.: 16/176,045

(22) Filed: Oct. 31, 2018

(65) Prior Publication Data

US 2019/0133776 A1 May 9, 2019

(30) Foreign Application Priority Data

Nov. 9, 2017 (KR) .................. 10-2017-0148543

(51) Int. Cl.
*A61F 2/44* (2006.01)
*A61B 17/70* (2006.01)
*A61F 2/28* (2006.01)
*A61F 2/46* (2006.01)
*A61F 2/30* (2006.01)

(52) U.S. Cl.
CPC ............ *A61F 2/442* (2013.01); *A61B 17/707* (2013.01); *A61F 2/446* (2013.01); *A61F 2/4455* (2013.01); *A61F 2/46* (2013.01); *A61F 2002/2835* (2013.01); *A61F 2002/308* (2013.01); *A61F 2002/3085* (2013.01); *A61F 2002/30136* (2013.01); *A61F 2002/30286* (2013.01); *A61F 2002/30563* (2013.01); *A61F 2002/448* (2013.01); *A61F 2220/0025* (2013.01)

(58) Field of Classification Search
CPC ............................................. A61F 2/44–447
USPC .......................................... 623/17.11–17.16
See application file for complete search history.

(56) References Cited

U.S. PATENT DOCUMENTS

| 5,669,909 A * | 9/1997 | Zdeblick | A61F 2/4611 606/247 |
| 5,928,284 A * | 7/1999 | Mehdizadeh | A61F 2/441 606/247 |
| 5,976,187 A * | 11/1999 | Richelsoph | A61F 2/446 623/17.16 |
| 7,147,665 B1 * | 12/2006 | Bryan | A61F 2/4425 623/17.16 |
| 8,771,358 B2 * | 7/2014 | Michelson | A61F 2/4455 623/17.16 |

(Continued)

FOREIGN PATENT DOCUMENTS

| JP | 2002-521090 A | 7/2002 |
| KR | 10-2006-0104336 A | 10/2006 |

(Continued)

*Primary Examiner* — Nicholas J Plionis
(74) *Attorney, Agent, or Firm* — Novick, Kim & Lee, PLLC; Jae Youn Kim

(57) ABSTRACT

Provided is a spinal implant. The spinal implant include an implant unit disposed between a vertebra (hereinafter, referred to as a 'first vertebra') and a neighboring vertebra (hereinafter, referred to as a 'second vertebra') and a buffer unit provided in the implant unit to disperse or absorb a pressure, an impact, or a load, which is applied from the first vertebra and the second vertebra. The spinal implant may promote bone fusion formation in the state of being inserted between the vertebra and the neighboring vertebra during the surgery and to promote the quickly recovery after the surgery and also may fulfill its role as a substitute for a damaged disk through the shape deformation and the restoration of the buffer unit after the surgical procedure.

4 Claims, 7 Drawing Sheets

(a)

(b)

(56) References Cited

U.S. PATENT DOCUMENTS 9,820,864 B2 * 11/2017 Fessler .................. A61F 2/446
2002/0049499 A1 * 4/2002 Walkenhorst ........... A61F 2/446
                                                                623/17.16

FOREIGN PATENT DOCUMENTS

KR    10-2013-0097206 A    9/2013
KR       10-1371418 B1    3/2014

* cited by examiner (a)

(b)

SPINAL IMPLANT

CROSS-REFERENCE TO RELATED APPLICATIONS

This U.S. non-provisional patent application claims priority under 35 U.S.C. § 119 of Korean Patent Application No. 10-2017-0148543, filed on Nov. 9, 2017, the entire contents of which are hereby incorporated by reference.

BACKGROUND

The present invention relates to a spinal implant, and more particularly, to a spinal implant which is capable of realizing rapid recovery after the procedure and promoting bone fusion formation in a state of being inserted between a vertebra and a neighboring vertebra and also fulfilling its role as a substitute for a damaged disk through shape deformation and restoration.

Since the conventional ventrotomy incision operation has a large incision site and a large amount of bleeding occurring during the surgery, there is a limitation that the patient's recovery is slow after the surgery. To solve this limitation, minimal invasive surgery (MIS) techniques using tools such as endoscopes have been developed.

The MIS may be a surgical technique in which a thin and long surgical instrument that is specifically designed to minimize an incision site required for the surgery is used to incise only a minimal part in the body surface of the patient.

Since the incision site required for the surgery is small, and the amount of blood loss during the surgery is small in the MIS compared to that of the laparotomy surgery, the recovery of the patent is fast, an external visible scar is small. As a result, the number of MIS is being remarkably increasing In recent years.

A disk existing between vertebrae functions as a joint and plays very important roles for minimizing an impact applied to the vertebrae while vertebral pulp accommodated inside the disk changes in position and shape according to the movement of the vertebra.

The vertebral pulp is mostly moisture (water). When we get older, an amount of moisture gradually decreases, and thus, a buffer function of a disc is lost.

As a result, when an excessive pressure is applied to the fibers, backache may occur. Here, if the excessive pressure is continuously applied, the fibers may be seriously stretched or ruptured to push nerve roots placed at a rear side thereof, thereby causing pains of pelvis, legs, and the like.

Thereafter, a distance between the vertebrae gradually decreases, or the vertebrae are collapsed to cause various kinds of side effects such as vertebral deformation.

There is a method, in which an intervertebral fusion cage, so-called, a cage is inserted between two adjacent vertebrae after a disc between the damaged vertebrae is removed, as a method for treating diseases involved due to the disc.

That is, the cage recovers the distance between the vertebrae to its original distance between the two adjacent vertebrae, which corresponds to an original height of the disc, thereby recovering the vertebral function.

The surgical method in which the cage is inserted between the vertebrae includes an anterior lumbar interbody fusion (ALIF) method in which a case is inserted from a front side of a vertebra after an abdominal operation, a lateral lumber interbody fusion (LLIF) method in which a cage is inserted through a side portion, a transforaminal lumbar interbody fusion (TLIF) method in which a case is inserted in a diagonal direction at a point that is spaced a distance of 30 mm to 40 mm laterally from a center of a back, a posterior lumbar interbody fusion (PLIF) method in which a cage is inserted from a back, and the like.

For example, there is an "intervertebral body fusion case" (hereinafter, referred to as a 'prior art') disclosed in Korean Patent Registration No. 10-1371418.

The prior art has a structure including: a vertical rear part; top and bottom surfaces respectively integrated with upper and lower portions of the rear part to face each other and extending to be gradually widened forward from the rear part; a top surface front part having a curvature that is convexly curved from an extension end of the top surface to the bottom surface; a bottom surface front part having a curvature that is convexly curved from an extension end of the bottom surface to the top surface; and a through hole for synostosis of the top and bottom surfaces.

However, most cases according to the prior art are vulnerable to torsion stress applied between the top and bottom surfaces and the rear part when a recipient perform motion such as twisting of his/her waist after the surgery. Also, when the cases are used for a long time, the cases are faced with a fatal problem such as breakage of the connection portion.

Thus, the damage due to the torsion stress may act as a factor that causes pain of the patient again. As a result, it is highly likely that the patient has to re-operate and thus suffers pain again.

PRIOR ART DOCUMENT

Patent Document

Patent Registration No. 10-1371418

SUMMARY

The present invention provides a spinal implant which is capable of realizing rapid recovery after the procedure and promoting bone fusion formation in a state of being inserted between a vertebra and a neighboring vertebra and also fulfilling its role as a substitute for a damaged disk through shape deformation and restoration.

An embodiment of the present invention provides a spinal implant including: an implant unit disposed between a vertebra (hereinafter, referred to as a 'first vertebra') and a neighboring vertebra (hereinafter, referred to as a 'second vertebra'); and a buffer unit disposed in the implant unit to disperse or absorb a pressure, an impact, or a load, which is applied from the first vertebra and the second vertebra.

The implant unit may include: a main body inserted between the first vertebra and the second vertebra from a back portion of a recipient; a screw thread screw-rotating along an outer circumferential surface of the main body in one direction; and an operation space defined in the main body from a rear end of the main boy to a front side of the main body, wherein the buffer unit may be disposed on the outer circumferential surface of the main body and in the operation space.

The buffer unit may include: a first buffer part comprising an operation space defined forward from an opened rear end of the implant unit to allow the operation space to communicate with an outer circumferential surface of the implant unit and permit shape deformation and restoration against the pressure, the impact, or the load, which is vertically applied to the implant unit between the first vertebra and the second vertebra; and a second buffer part having both ends connected and fixed to an inner surface of the implant unit, which defines the operation space, to permit the shape deformation and the restoration against the pressure, the impact, or the load, which is vertically applied to the implant unit between the first vertebra and the second vertebra.

The screw thread may include: a small diameter part disposed at a front end and a rear end of the main body and having a first outer diameter; and a large diameter part disposed between the front end and the rear end of the main body and having a second outer diameter greater than the first outer diameter, wherein, in a virtual line passing through a center of the main body in a forward and backward direction, a first distance of the virtual line from the large diameter part to the rear end of the main body may be equal to or greater than a second distance of the virtual line from the front end of the main body to the large diameter part.

The first buffer part may include a deformation notch that is cut to be gradually narrowed from both sides of the opened rear end of the implant unit to the front side of the implant unit.

The second buffer part may include: a first protrusion piece defining one end of both ends, which are connected and fixed to an inner surface of the implant unit, and connected to an inner surface of the rear side of the implant unit; a second protrusion piece defining the other end of both ends, which are connected and fixed to the inner surface of the implant unit, and connected to an inner surface of the front side of the implant unit; and a connection deformation assembly built in the operation space while connecting the first protrusion piece to the second protrusion piece and changing torque according to first force applied from an end of the first protrusion piece and second force applied from the end of the second protrusion piece into the elastic force.

The spinal implant may further include an operation space defined in the inside forward from an opened rear end of the implant unit and at least one bone fusion slot having a predetermined length and penetrated to allow the operation space to communicate with both sides of an outer circumferential surface of the implant unit, wherein a portion of the buffer unit may be provided from a vicinity of a rear side of the bone fusion slot to the rear end of the implant unit.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
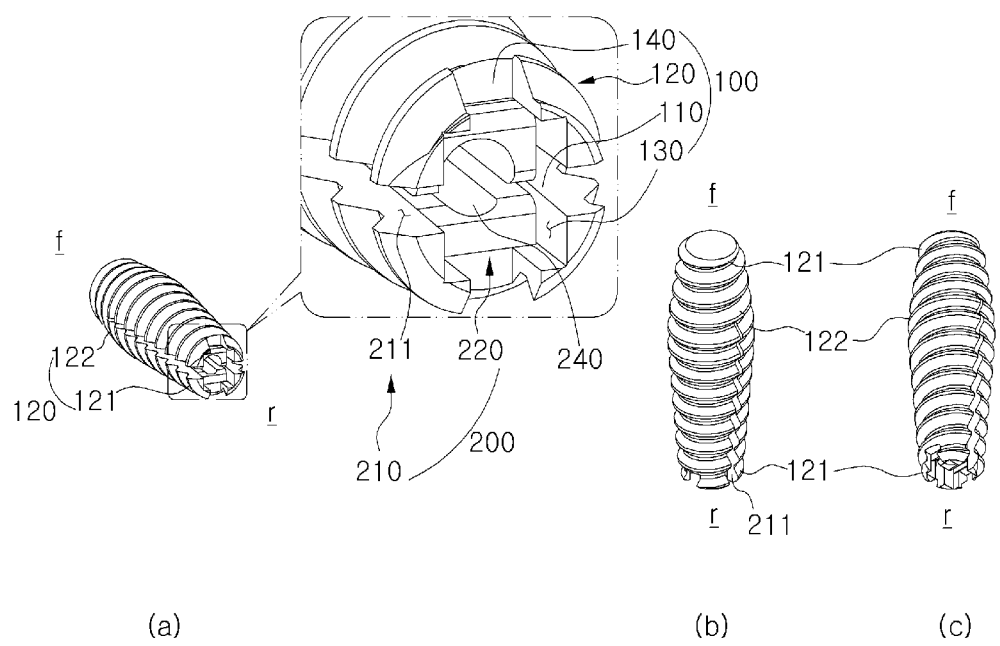
FIG. 1 is a conceptual perspective view illustrating an overall outer appearance of a spinal implant when viewed at various angles according to an embodiment of the present invention.

Advantages and features of the present disclosure, and implementation methods thereof will be clarified through following embodiments described with reference to the accompanying drawings.

The present invention may, however, be embodied in different forms and should not be construed as limited to the embodiments set forth herein.

In this specification, these embodiments are provided so that this disclosure will be thorough and complete, and will fully convey the scope of the present invention to those skilled in the art.

Also, the present invention is only defined by scopes of claims.

Accordingly, in some embodiments, well-known components, well-known device operations, and well-known techniques will not be described in detail to avoid ambiguous interpretation of the present invention.

Also, like reference numerals refer to like elements throughout. In the following description, the technical terms are used (mentioned) only for explaining a specific exemplary embodiment while not limiting the present disclosure.

The terms of a singular form may include plural forms unless referred to the contrary. The meaning of "include," "comprise," "including," or "comprising," specifies a component and an operation but does not exclude other components and operations.

Unless terms used in the present invention are defined differently, all terms (including technical and scientific terms) used in this specification have the same meaning as generally understood by those skilled in the art.

Also, unless defined apparently in the description, the terms as defined in a commonly used dictionary are not ideally or excessively construed as having formal meaning.

Hereinafter, preferred embodiments of the present invention will be described in more detail with reference to the accompanying drawings.

Figure 2:
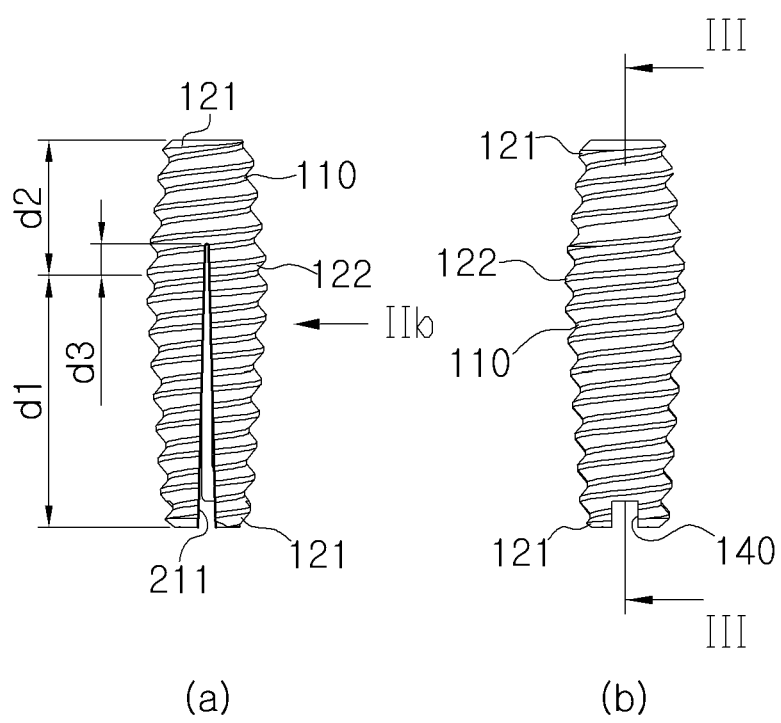
FIG. 2 is a conceptual side view illustrating an outer appearance of the spinal implant when viewed at various angles according to an embodiment of the present invention.

FIG. 1 is a conceptual perspective view illustrating an overall outer appearance of a spinal implant when viewed at various angles according to an embodiment of the present invention, and FIG. 2 is a conceptual side view illustrating an outer appearance of the spinal implant when viewed at various angles according to an embodiment of the present invention.

Figure 3:
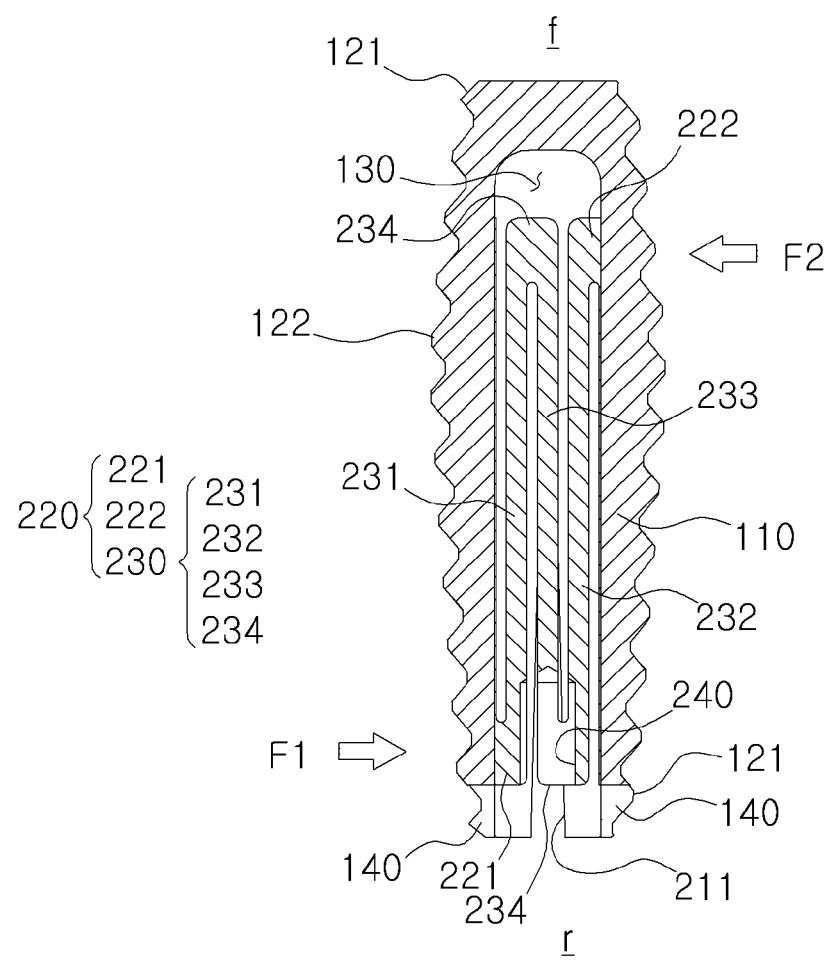
FIG. 3 is a conceptual internal cross-sectional view taken along line III-III of FIG. 2.

Also, FIG. 3 is a conceptual internal cross-sectional view taken along line III-III of FIG. 2.

Figure 4:
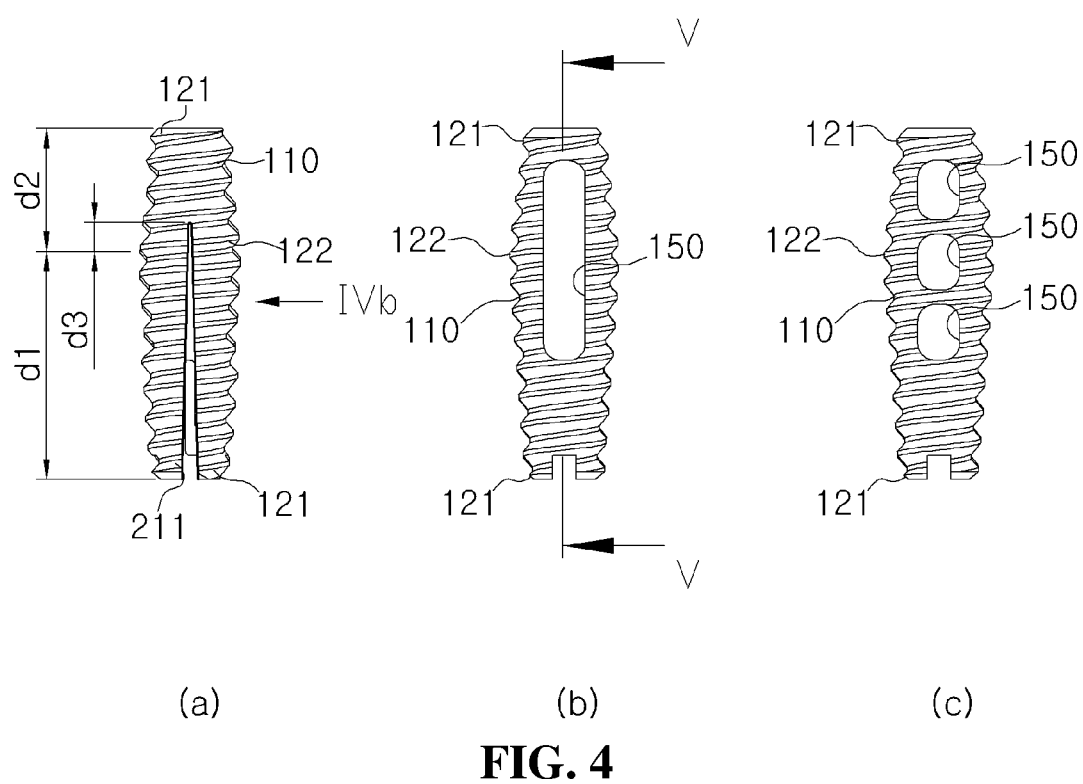
FIG. 4 is a conceptual perspective view illustrating an outer appearance of a spinal implant when viewed at various angles according to another embodiment of the present invention.
Figure 5:
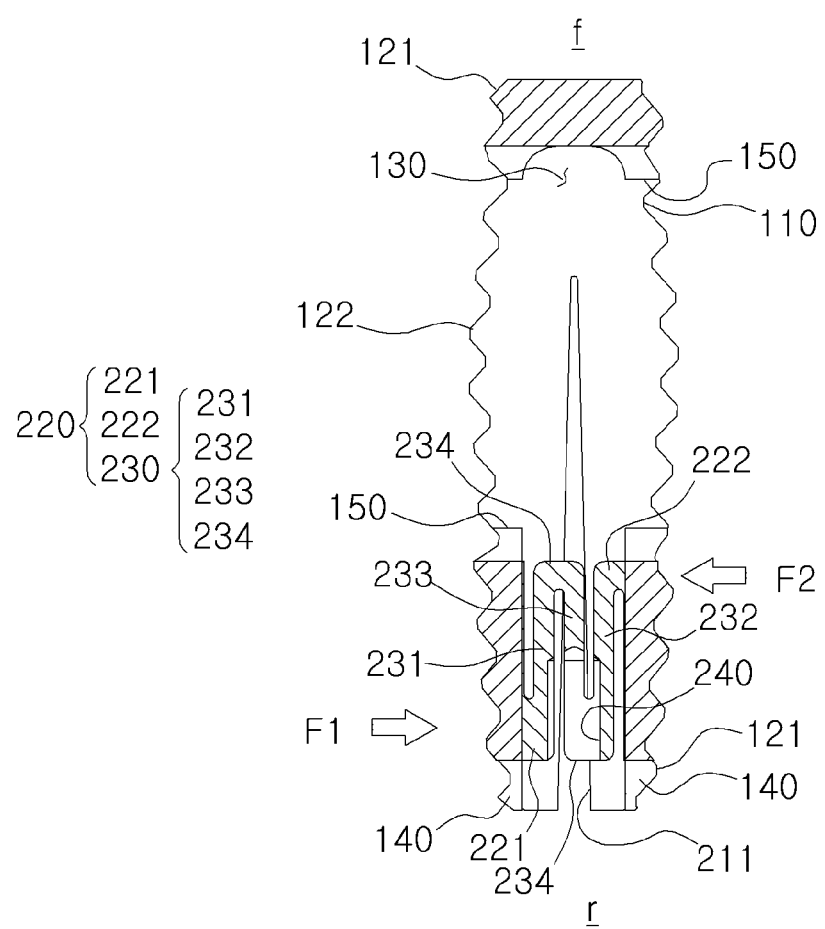
FIG. 5 is a conceptual internal cross-sectional view taken along lien V-V of FIG. 4.

FIG. 4 is a conceptual perspective view illustrating an outer appearance of a spinal implant when viewed at various angles according to another embodiment of the present invention, and FIG. 5 is a conceptual internal cross-sectional view taken along lien V-V of FIG. 4.

Figure 6:
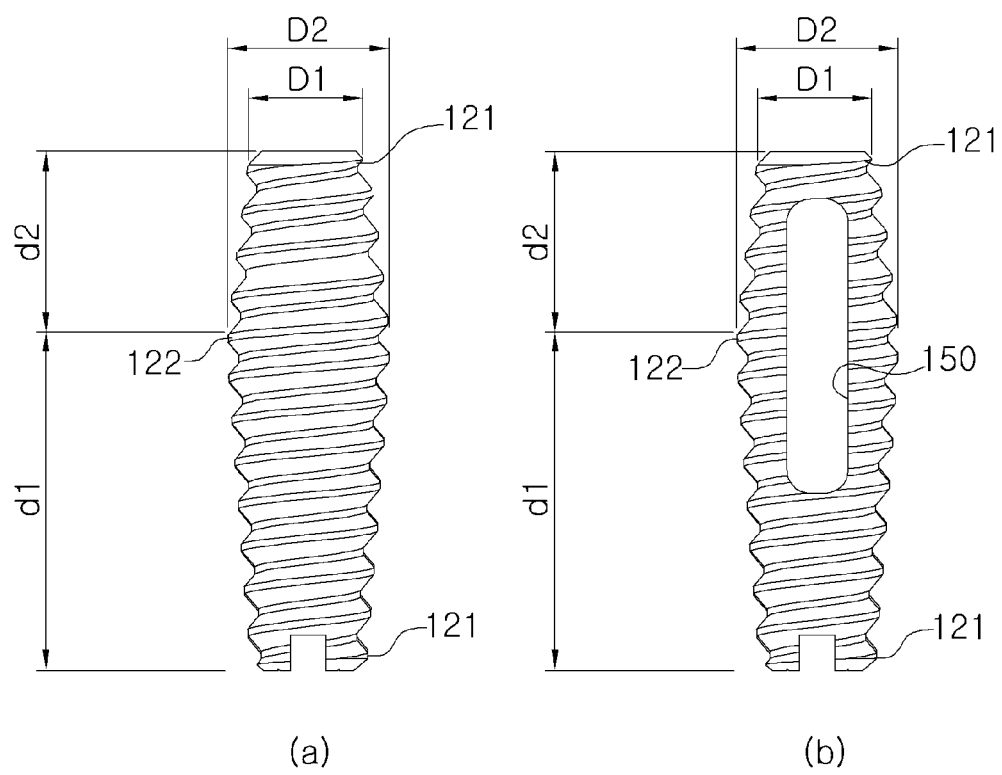
FIG. 6 is a conceptual side view illustrating the outer appearances of the spinal implants according to an embodiment and another embodiment of the present invention.

Also, FIG. 6 is a conceptual side view illustrating the outer appearances of the spinal implants according to an embodiment and another embodiment of the present invention.

Figure 7:
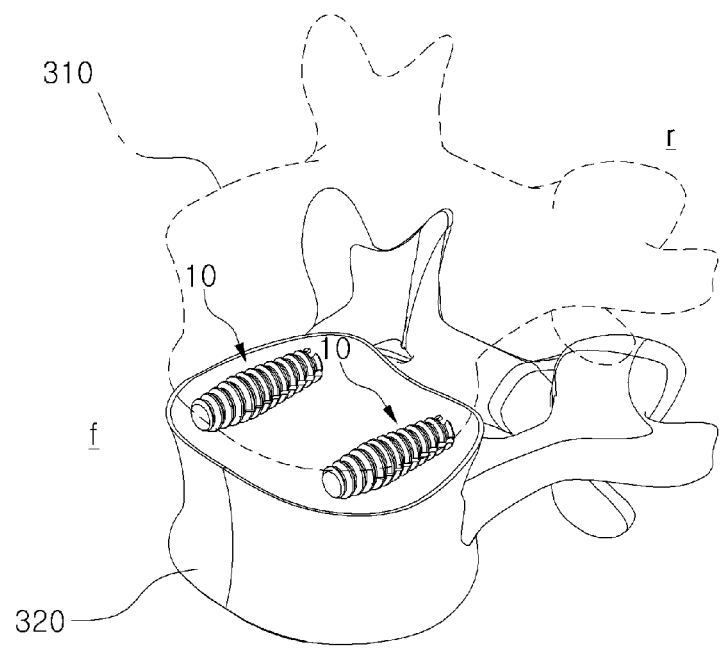
FIG. 7 is a conceptual perspective view illustrating a surgical procedure state in which a spinal implant is inserted between a first vertebra and a second vertebra according to a preferred embodiment of the present invention.
Figure 7:
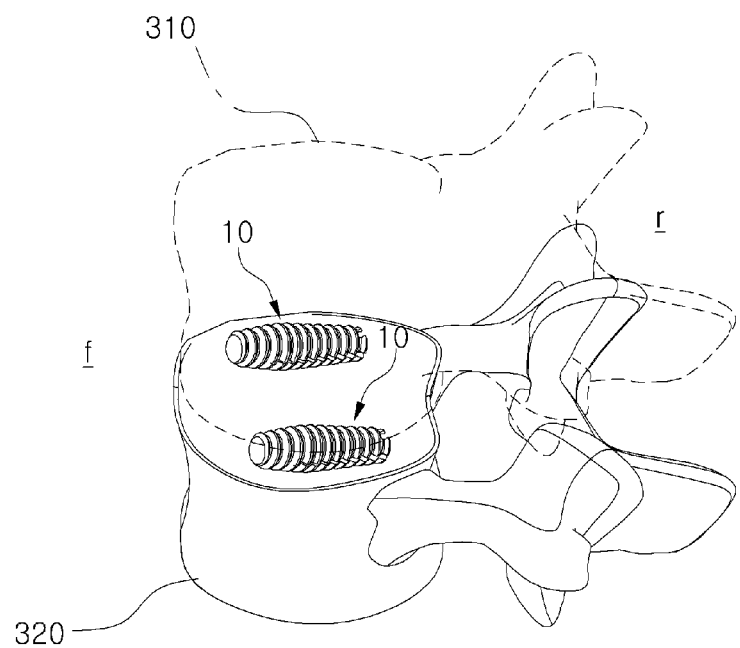

Also, FIG. 7 is a conceptual perspective view illustrating a surgical procedure state in which a spinal implant is inserted between a first vertebra and a second vertebra according to a preferred embodiment of the present invention.

For reference, in the drawings, "f" represents a front side, and "r" represents to a rear side. Also, a virtual line passing through a center of a main body, which will be described later, in a front and rear direction will be defined as a straight line extending along the line III-III of FIG. 2 and the line V-V of FIG. 4.

As illustrated in the drawings, the spinal implant according to the present invention may include an implant unit 100 disposed between a vertebra (hereinafter, referred to as a 'first vertebra 310' and a neighboring vertebra (hereinafter, referred to as a 'second vertebra 320') and a buffer unit 200 disposed in the implant unit 100 to disperse or absorb a pressure, an impact, or a load, which is applied from the first vertebra 310 and the second vertebra 320.

The foregoing embodiment as well as following various embodiments may be applied to the present invention.

The implant unit 100 may include a main body 110 inserted between the first vertebra 310 and the second vertebra 320 from a back portion of a recipient, a screw thread screw-rotating along an outer circumferential surface of the main body 110 in one direction, and an operation space 130 defined in the main body 110 from a rear end of the main boy 110 to a front side of the main body 110.

Here, the buffer unit 200 that will be described later may be disposed on the outer circumferential surface of the main body 110 and in the operation space 130.

Thus, the spinal implant 10 including the implant unit 100 provided with the buffer unit 200 may be inserted from the front end of the main body 110 through an opening (not shown) defined in the back portion of the recipient and then be seated and fixed between the first and second vertebrae 310 and 320 as illustrated in FIG. 7.

More particularly, referring to FIGS. 1 to 5, the buffer unit 200 may include a first buffer part 210 and a second buffer part 220 in a broad sense.

First, the first buffer part 210 may include an operation space defined forward from the opened rear end of the implant unit 100 and be provided to allow the operation space to communicate with the outer circumferential surface of the implant unit 100 and permit shape deformation and restoration against the pressure, the impact, or the load, which is vertically applied to the implant unit 100 between the first vertebra 310 and the second vertebra 320.

The second buffer part 220 may have both ends connected and fixed to an inner surface of the implant unit 100, which defines the operation space 130, and permit shape deformation and restoration against the pressure, the impact, or the load, which is vertically applied to the implant unit between the first vertebra 310 and the second vertebra 320.

The first and second buffer parts 210 and 220 will be described again in detail.

More particularly, referring to FIGS. 2, 4, and 6, the screw thread 120 may include a small diameter part 121 and a large diameter part 122 in a broad sense.

Here, the small diameter part 121 is disposed between a front end and a rear end of the main body 110 and has a first outer diameter D1.

The large diameter part 122 is disposed between the front end and the rear end of the main body 110 and has a second diameter D2 greater than the first outer diameter D1.

Thus, in a virtual line passing through a center of the main body 110 in the front and rear direction, a first distance d1 of the virtual line from the large diameter part 122 to the rear end of the main body 110 may be equal to or greater than a second distance d2 from the front end of the main body 110 to the large diameter part 122.

Particularly, when the first distance D1 is greater than the second distance D2, it is preferable and useful that the first and second vertebrae 310 and 320 are reliably fixed to correspond to shapes of surfaces facing each other.

Furthermore, the outer diameter from the front end of the main body 110 to the large diameter part 122 may gradually increase, and the outer diameter from the large diameter part 122 to the rear end of the main body 110 may gradually decrease. Thus, when respective points at predetermined positions on a circumference of the outer diameters are connected to each other in a longitudinal direction from the front side to the rear side of the main body 110, the screw thread may have a streamlined shape as a whole.

Thus, the overall shape of the main body 110 may have a curved and rounded shape that is abruptly somewhat from the front end to the large diameter part 122 and also have a curved surface that is gentle somewhat from the large diameter part 122 to the rear end. Thus, the main body 110 may have a shape that is reminiscent of an outer appearance of a cigar.

The first buffer part 210 may include a deformation notch 211 that is cut to be gradually narrowed from both sides of the opened rear end of the implant unit 100 to the front side of the implant unit 100.

Here, referring to FIGS. 2 and 4, the front end of the deformation notch 211 may be disposed between the front end of the implant unit 100 and the large diameter part 122.

Particularly, in a virtual line passing through the center of the implant unit 100 in the front and rear direction, a third distance d3 of the virtual line from a front end of the deformation notch 211 to the large diameter part 122 may be ⅕ to ½ of the second distance d2 of the virtual line from the front end of the main body 110 to the large diameter part 122.

That is, when the third distance d3 is less than ⅕ of the second distance d2, since much force is required for the shape deformation and the restoration due to the deformation notch 211, the buffering effect due to the implant unit 100 itself may be deteriorated.

When the third distance d3 exceeds ½ of the second distance d2, deformation and damage by fatigue failure around the front end of the deformation notch 211 due to the pressure, the load, or the impact, which is vertically applied to the implant unit 100 between the first vertebra 310 and the second vertebra 320, may occur to significantly deteriorate the durability of the implant unit 100.

Also, when assuming another virtual line perpendicular to the virtual line connecting the rear ends of the deformation notches 211 disposed on both sides of the outer circumferential surface of the implant unit 100 to each other, a tool coupling groove 140 recessed from each of both sides of the rear end of the implant unit 100 and engaged with an end of the surgical operation tool (not shown) may be further provided.

More particularly, referring to FIGS. 3 and 5, the second buffer part 220 may also be applied to a structure including first and second protrusion pieces 221 and 222 and a connection deformation assembly 230 in a broad sense.

Here, the first protrusion piece 221 may define one end of both ends connected and fixed to the inner surface of the implant unit 100 and be connected to an inner surface of the rear side of the implant unit 100.

Also, the second protrusion piece 222 may define the other end of both ends connected and fixed to the inner surface of the implant unit 100 and be connected to an inner surface of the front side of the implant unit 100.

In addition, the connection deformation assembly 230 may be built in the operation space 30 while connecting the first protrusion piece 221 to the second protrusion piece 222 to change torque according to first force F1 applied from the end of the first protrusion piece and second force F2 applied from the end of the second protrusion piece into elastic force.

Furthermore, more particularly, the above-described connection deformation assembly 230 may include a first support piece 231 having a rear end connected to the end of the first protrusion piece 221 and built in the operation space 130 and having a predetermined length in the front and rear direction of the implant nit 100.

Also, the above-described connection deformation assembly 230 may include a second support piece 232 having a front end connected to the end of the second protrusion piece 222 and disposed in parallel to the first support piece 231 and built in the operation space 130.

Also, the above-described connection deformation assembly 230 may include 2n−1 (where n is a positive integer equal to or greater than 1) intermediate support piece 233 disposed in parallel to each other between the first support piece 231 and the second support piece 232 and built in the operation space 130.

Furthermore, the above-described connection deformation assembly 230 may include a connection piece 234 connecting the front end of the first support piece 231 to one end of the intermediate support piece 233 and connecting the rear end of the second support piece 232 to the other end of the intermediate support piece 233 to allow the second buffer part 220 to form a zigzag shape from the first protrusion piece 221 to the second protrusion piece 222.

Thus, the torque continuously generated by being interlocked with the first and second force F1 and F2 by the connection deformation assembly 230 having the zigzag shape as a whole may be elastically dispersed and supported to perform the buffering function having almost the same performance as the patient's own disk, thereby helping the normal life of the patient.

Also, the second buffer part 220 may further have a tool coupling hole 240 that is recessed with a predetermined width or diameter and a predetermined length from the rear end of the connection deformation assembly 230 to the front side of the implant unit 100 so that an end of the surgical operation tool is inserted and fixed together with the above-described tool coupling groove 140 for the surgical convenience of the practitioner.

As illustrated in FIGS. 4 to 6, the present invention may further include an operation space 130 defined forward from the opened rear end of the implant unit 100 and at least one bone fusion slot 150 that has a predetermined length and is penetrated to allow the operation space 130 to communicate with both sides of the outer circumferential surface of the implant unit 100.

It is seen that a portion of the buffer unit 200 may be provided from the vicinity of a rear end of the bone fusion slot 150 to the rear end of the implant unit 100.

Thus, an autologous bone fragment or artificial bone substitute may be filled into the operation space 130 through the bone fusion slot 150 to quickly perform bone fusion and bone generation.

Hereinafter, the operation and effect of the spinal implant according to the preferred embodiment of the present invention will be described as follows.

First, the present invention may include the implant unit 100 disposed between the first vertebra and the second vertebra and the buffer unit 200 provided in the implant unit 100 to disperse or absorb the pressure, the impact, or the load, which is applied from the first vertebra and the second vertebra. Since the implant unit fulfills its role as the substitute for the damaged disk through the shape deformation and the restoration of the buffer unit after the surgical procedure, the implant unit may help the patient's normal life.

Also, the implant unit 100 according to the present invention may include the main body 110 inserted between the first vertebra 310 and the second vertebra 320 from the back portion of the recipient, the screw thread 120 screw-rotating along the outer circumferential surface of the main body 110 in one direction, and the operation space 130 defined in the main body 110 from the rear end of the main body 110 toward the front side of the main body 110. The buffer unit 200 may be disposed on the outer circumferential surface of the main body 110 and in the operation space 130. Thus, even if the buffer unit 200 performing the repetitive operation that permits the shape deformation and the restoration is provided, the portion of the implant unit 100, which is exposed to the outside, may be minimized as a whole to realize the compactness of the entire device and to improve the strength and the durability of the entire device.

Also, the buffer unit 200 according to the present invention may include the operation space 130 defined forward from the opened rear end of the implant unit 100, the first buffer part 210 allowing the operation space 130 to communicate with the outer circumferential surface of the implant unit 100 and permitting the shape deformation and the restoration against the pressure, the impact, or the load, which is vertically applied to the implant unit 100 between the first vertebra 310 and the second vertebra 320, and a second buffer part 220 having both ends connected and fixed to the inner surface of the implant unit 100, which defines the operation space 130, and permitting the shape deformation and the restoration against the pressure, the impact, or the load, which is vertically applied to the implant unit 100 between the first vertebra 310 and the second vertebra 320. Thus, even if the repetitive operation that permits the shape deformation and the restoration is performed, the structural strength and the durability may be maintained for a long time to help the patient's normal life.

Also, the screw thread 120 according to the present invention may include the small diameter part 121 disposed between the front end and the rear end of the main body 110 and having the first outer diameter D1 and the large diameter part 122 disposed between the front end and the rear end of the main body 110 and having the second outer diameter D2 greater than the first outer diameter D1. In the virtual line passing through the center of the main body 110 in the forward and backward direction, the first distance d1 of the virtual line from the large diameter part 122 to the rear end of the main body 110 may be equal to or greater than the second distance d2 of the virtual line from the front end of the main body 110 to the large diameter part 122. Thus, the ergonomic structure which is seated and fixed to well correspond to the shape of each of the facing surfaces between the general first and second vertebrae 310 and 320 may be provided to obtain the superior procedure result.

Also, the first buffer part 210 according present invention may include the deformation notch 211 that is cut to be gradually narrowed from each of both sides of the opened rear end of the implant unit 100 to the front side of the implant unit 100. Even if the repetitive operation that permits the shape deformation and the restoration is performed, the structural strength and the durability may be maintained for a long time to help the patient's normal life.

Also, the second buffer part 220 according to the present invention may include the first protrusion piece 221 defining one end of both ends, which are connected and fixed to the inner surface of the implant unit 100, and connected to the inner surface of the rear side of the implant unit 100, a second protrusion piece 222 defining the other end of both ends, which are connected and fixed to the inner surface of the implant unit 100, and connected to the inner surface of the front side of the implant unit 100, and the connection deformation assembly 230 built in the operation space 130 while connecting the first protrusion piece 221 to the second protrusion piece 222 and changing the torque according to the first force F1 applied from the end of the first protrusion piece 221 and the second force F2 applied from the end of the second protrusion piece 222 into the elastic force. Thus, the torsional stress due to the generation of the torque may be effectively dispersed to improve the durability and the structural strength of the entire device.

Also, according to the present invention, the implant unit 100 may the operation space defined forward from the opened rear end of the implant unit 100 and the at least one bone fusion slot 150 that has the predetermined length and is penetrated to allow the operation space 130 to communicate with both sides of the outer circumferential surface of the implant unit 100. A portion of the buffer unit 200 may be provided from the vicinity of the rear side of the bone fusion slot 150 to the rear end of the implant unit 199 to promote the bone fusion formation in the state of being inserted between the vertebra and the neighboring vertebra during the surgery and to promote the quickly recovery after the surgery.

As described above, the basic technical idea of the present invention may provide the spinal implant which is capable of realizing the rapid recovery after the procedure and promoting the bone fusion formation in the state of being inserted between the vertebra and the neighboring vertebra and also fulfilling its role as the substitute for the damaged disk through shape deformation and restoration.

According to the present invention having the above-described constitutions, the following effects may be attained.

First, the present invention may include the implant unit disposed between the vertebra (hereinafter, referred to as the 'first vertebra') and the neighboring vertebra (hereinafter, referred to as the 'second vertebra') and a buffer unit provided in the implant unit to disperse or absorb the pressure, the impact, or the load, which is applied from the first vertebra and the second vertebra. Since the implant unit fulfills its role as the substitute for the damaged disk through the shape deformation and the restoration of the buffer unit after the surgical procedure, the implant unit may help the patient's normal life.

Also, the implant unit according to the present invention may include the main body inserted between the first vertebra and the second vertebra from the back portion of the recipient, the screw thread screw-rotating along the outer circumferential surface of the main body in one direction, and the operation space defined in the main body from the rear end of the main body toward the front side of the main body. The buffer unit may be disposed on the outer circumferential surface of the main body and in the operation space. Thus, even if the buffer unit performing the repetitive operation that permits the shape deformation and the restoration is provided, the portion of the implant unit, which is exposed to the outside, may be minimized as a whole to realize the compactness of the entire device and to improve the strength and the durability of the entire device.

Also, the buffer unit according to the present invention may include the operation space defined forward from the opened rear end of the implant unit, the first buffer part allowing the operation space to communicate with the outer circumferential surface of the implant unit and permitting the shape deformation and the restoration against the pressure, the impact, or the load, which is vertically applied to the implant unit between the first vertebra and the second vertebra, and a second buffer part having both ends connected and fixed to the inner surface of the implant unit, which defines the operation space, and permitting the shape deformation and the restoration against the pressure, the impact, or the load, which is vertically applied to the implant unit between the first vertebra and the second vertebra. Thus, even if the repetitive operation that permits the shape deformation and the restoration is performed, the structural strength and the durability may be maintained for a long time to help the patient's normal life.

Also, the screw thread according to the present invention may include the small diameter part disposed between the front end and the rear end of the main body and having the first outer diameter and the large diameter part disposed between the front end and the rear end of the main body and having the second outer diameter greater than the first outer diameter. In the virtual line passing through the center of the main body in the forward and backward direction, the first distance of the virtual line from the large diameter part to the rear end of the main body may be equal to or greater than the second distance of the virtual line from the front end of the main body to the large diameter part. Thus, the ergonomic structure which is seated and fixed to well correspond to the shape of each of the facing surfaces between the general first and second vertebrae may be provided to obtain the superior procedure result.

Also, the first buffer part according to the present invention may include a deformation notch that is cut to be gradually narrowed from each of both sides of the opened rear end of the implant unit to the front side of the implant unit. Even if the repetitive operation that permits the shape deformation and the restoration is performed, the structural strength and the durability may be maintained for a long time to help the patient's normal life.

Also, the second buffer part according to the present invention may include the first protrusion piece defining one end of both ends, which are connected and fixed to the inner surface of the implant unit, and connected to the inner surface of the rear side of the implant unit, a second protrusion piece defining the other end of both ends, which are connected and fixed to the inner surface of the implant unit, and connected to the inner surface of the front side of the implant unit, and a connection deformation assembly built in the operation space while connecting the first protrusion piece to the second protrusion piece and changing torque according to the first force applied from the end of the first protrusion piece and the second force applied from the end of the second protrusion piece into elastic force. Thus, torsional stress due to the generation of the torque may be effectively dispersed to improve the durability and the structural strength of the entire device.

Also, according to the present invention, the implant unit may include the operation space defined forward from the opened rear end of the implant unit and the at least one bone fusion slot that has the predetermined length and is penetrated to allow the operation space to communicate with both sides of the outer circumferential surface of the implant unit. A portion of the buffer unit may be provided from the vicinity of the rear side of the bone fusion slot to the rear end of the implant unit to promote the bone fusion formation in the state of being inserted between the vertebra and the neighboring vertebra during the surgery and to promote the quickly recovery after the surgery.

Furthermore, when compared with the typical procedure in which the implant may be damaged in the case in which the implant is inserted between the vertebra and the neighboring vertebra by using the hammer, according to the present invention, the implant may be inserted while rotating by using the surgical tool inserted and coupled from the rear side from the implant unit. Therefore, the implant may be safely conveniently inserted.

Also, according to the present invention, since the implant is stably seated and coupled between the vertebra and the neighboring vertebra by using the structure of the screw thread formed along the outer circumferential surface of the main body in one direction, the possibility of separation of the movement of the recipient may be very small, and the rapid stabilization between the vertebra and the neighboring vertebra may be achieved.

Also, it should be understood that numerous other modifications and embodiments can be devised by those skilled in the art that will fall within the scope of the fundamental technical idea of the principles of the present invention.

What is claimed is:

1. A spinal implant comprising:
   an implant unit configured to be disposed between a first vertebra and a second vertebra adjacent to the first vertebra; and
   a buffer unit configured to be disposed in the implant unit to disperse or absorb a pressure, an impact, or a load, which is applied from the first vertebra and the second vertebra,
   wherein the implant unit includes:
   a main body configured to be inserted between the first vertebra and the second vertebra from a back portion of a recipient;
   a screw thread arranged along an outer circumferential surface of the main body in one direction; and
   an operation space defined in the main body from a rear end of the main body to a front side of the main body, the buffer unit being configured to be disposed in the operation space,
   wherein the screw thread includes a larger diameter part disposed between the front end and the rear end of the main body and having a greatest outer diameter,
   wherein, in a virtual line passing through a center of the main body in a longitudinal direction of the main body, a first distance of the virtual line from the larger diameter part to the rear end of the main body is equal to or greater than a second distance of the virtual line from the front end of the main body to the larger diameter part,
   wherein a deformation notch is formed on the implant unit to be penetrated to allow the operation space to communicate with an outside of the implant unit and extends from the rear end of the main body to a front end of the deformation notch in the longitudinal direction of the main body, the deformation notch being gradually narrowed from the rear end of the main body to the front end of the deformation notch,
   wherein the front end of the deformation notch is located between the front end of the main body and the larger diameter part, and
   wherein a third distance of the virtual line from the front end of the deformation notch to the large diameter part is ⅕ to ½ of the second distance of the virtual line.

2. The spinal implant of claim 1, wherein the buffer unit comprises:
   a first protrusion piece configured to be connected and fixed to an inner surface of the implant unit at an inner surface of the rear side of the implant unit;
   a second protrusion piece configured to be connected and fixed to the inner surface of the implant unit at an inner surface of the front side of the implant unit; and
   a connection deformation assembly configured to be disposed in the operation space while connecting the first protrusion piece to the second protrusion piece so as to elastically respond to torque applied from an end of the first protrusion piece or an end of the second protrusion piece.

3. The spinal implant of claim 2, wherein the connection deformation assembly comprises:
   a first support piece connected to the first protrusion piece and extending in the longitudinal direction toward the front end of the main body;
   a second support piece connected to the second protrusion piece and extending in the longitudinal direction toward the read end of the main body; and
   at least one intermediate support piece connecting the first support piece and the second support piece,
   wherein the first support piece, the second support piece, and the at least one intermediate support piece are arranged in a zigzag shape when disposed in the operation space.

4. The spinal implant of claim 1, further comprising at least one bone fusion slot having a predetermined length and penetrated to allow the operation space to communicate with the outside of the implant unit.

* * * * *